United States Patent [19]

Bronskill et al.

[11] Patent Number: 4,838,677

[45] Date of Patent: Jun. 13, 1989

[54] EYE EXERCISING DEVICES

[75] Inventors: Michael J. Bronskill, Toronto, Canada; Bai-Chuan Jiang, Shanghai, China

[73] Assignee: Ayetech Inc., Willowdale, Canada

[21] Appl. No.: 34,951

[22] Filed: Apr. 6, 1987

[51] Int. Cl.$^4$ .................................... A61B 3/00

[52] U.S. Cl. .................................... 351/203

[58] Field of Search ............... 351/200, 203, 205, 211, 351/221

[56] References Cited

U.S. PATENT DOCUMENTS

| | | | |
|---|---|---|---|
| 2,422,384 | 6/1947 | Alexander | 128/76.5 |
| 3,774,599 | 11/1973 | Martin . | |
| 3,843,240 | 10/1974 | Cornsweet | 351/2 |
| 3,875,934 | 4/1975 | Sadanaga | 128/76.5 |
| 4,408,846 | 10/1983 | Balliet | 351/203 |
| 4,464,027 | 8/1984 | Cooper | 351/203 |
| 4,506,963 | 3/1985 | Cooper | 351/203 |
| 4,533,221 | 8/1985 | Trachtman | 351/203 |
| 4,660,945 | 4/1987 | Trachtman . | |

FOREIGN PATENT DOCUMENTS

| | | |
|---|---|---|
| 135736 | 4/1985 | European Pat. Off. . |
| 164439 | 12/1985 | European Pat. Off. . |
| 442956 | 2/1936 | United Kingdom . |
| 711326 | 6/1954 | United Kingdom . |

OTHER PUBLICATIONS

Jiang Bai-Chuan, Improvement of Accommodation Function by Accommodative Training, a paper presented at proceedings of the Chinese Physiological Society Conference, 1985.

*Primary Examiner*—Rodney B. Bovernick
*Assistant Examiner*—Paul Dzierzynski
*Attorney, Agent, or Firm*—Fleit, Jacobson, Cohn & Price

[57] ABSTRACT

An eye exercising device is disclosed having a positioning product to position the eye along an optical axis, which defines a range of accommodation for the eye. The range of accommodation is bounded by a proximal and a distal limit. An object is movable along the optical path and a displacement device is provided to displace continuously the object along the optical path from a first location on one side of a given one of the limits to a second location on another side of the given limit opposite the first location.

21 Claims, 2 Drawing Sheets

EYE EXERCISING DEVICES

This invention relates to eye exercising devices.

The ability of the eye to focus an image sharply on the retina of objects at various distances is characterized by its range of accommodation. It is not uncommon for the eye to be unable to focus clearly for distant objects, a condition known as myopia. This condition can be due to a variety of causes such as the inherent shape of the lens of the eye and the shape of the eye itself. The contraction and relaxation of the ciliary muscle control, to some extent, the shape of the lens of the eye. A condition known as pseudomyopia can exist wherein the ciliary muscle is unable to relax completely, thereby preventing the lens of the eye from attaining its flattest shape and, thus, the eye from focusing on distant objects.

Control of the ciliary muscle is governed by a large variety of visual stimuli or cues. Of these cues, there are several which are particularly important, including (i) the change in size of the image on the retina which usually accompanies the change in distance of the object from the eye, and (ii) the blur of the image which serves, through chromatic or spherical aberrations, to provide an indication or error signal to the ciliary muscle to control focusing. This blur cue is influenced by both the brightness and detail of the object upon which the eye is focusing.

Myopia is commonly alleviated by the placement of a corrective divergent lens in front of the eye. Although satisfactory in providing improved ability to focus on distant objects, the use of such a lens does not improve, and, in many cases, decreases the accommodative range of the eye.

In recent years it has been the belief that exercising the ciliary muscle may alleviate pseudomyopia, particularly in juveniles. Accordingly, several techniques have been proposed in an attempt to exercise the eye, so as to improve the eye's visual acuity. For example, one technique provides an image which is placed at one of a number of preselected locations, with a lens placed in front of the eye, according to the Badal principle. The subject is then instructed to identify the image by causing the eye to focus on the object. However, this procedure does not enable the eye to be exercised continually and is therefore not as effective as desired in restoring the activity of the ciliary muscle.

Moreover, such a procedure does not enable the eye to respond to a transition from a focused image to a blurred image on the retina and vice versa. This is due to the fact that such a transition has not been recognized as a significant stimulus to restore the activity of the ciliary muscle.

Accordingly, the object of the present invention is to provide a novel device and technique for exercising the eye.

Broadly stated the invention comprises an eye exercising device comprising:

positioning means to position said eye along an optical path, said optical path defining a range of accommodation for said eye, said range of accommodation bounded by a proximal limit and a distal limit;

an object movable along said optical path;

displacement means to displace continuously said object along said optical path from a first location on one side of a given one of said limits and beyond said range to a second location on another side of said given limit opposite said first location.

In one embodiment of the present invention the object includes a uniformly illuminated slide photograph.

In another embodiment of the present invention, the object includes a plate having formed thereon a passage and an illumination means for casting a beam of light on said plate.

In another aspect of the present invention, there is provided a method of exercising an eye comprising the steps of:

positioning said eye along an optical path, said optical path defining a range of accommodation of said eye, said range of accommodation bounded by a proximal limit and a distal limit;

providing an object on said optical path; and displacing said object along said optical path from a first location on one side of a given one of said limits and beyond said range to a second location on another side of said given limit opposite said first location, said step of defining a transition wherein said object passes said given limit while being focused by said eye.

Further features, objects and advantages of the present invention will become evident following a detailed description of several preferred embodiments, given by way of example only, and as seen in the following drawings in which.

Figure 1:
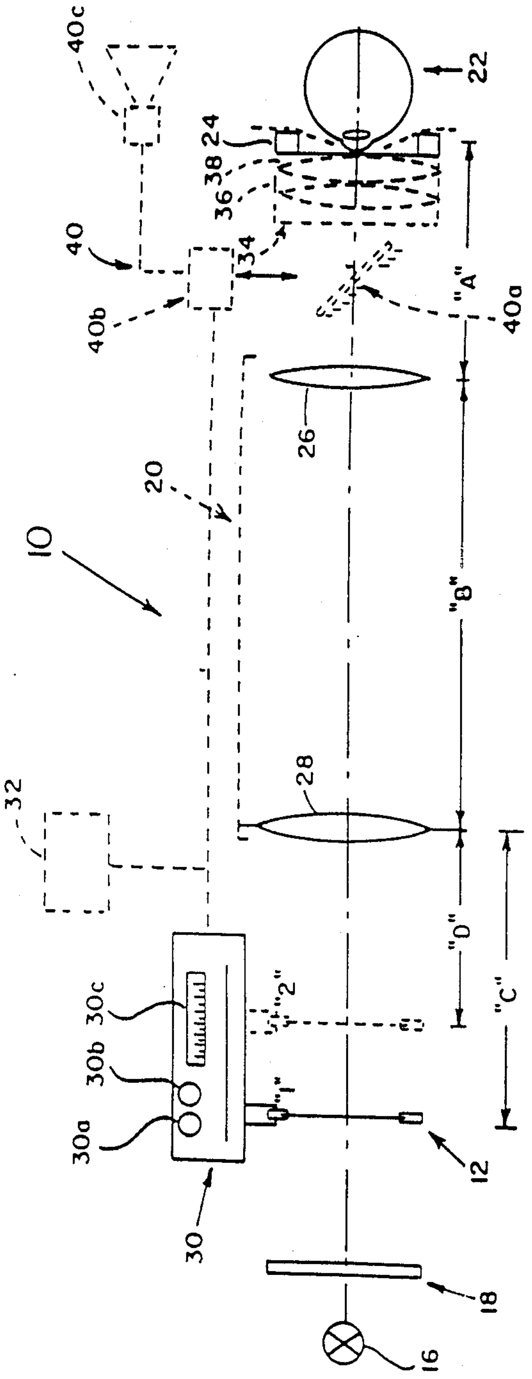
FIG. 1 is a schematic view of an eye exercising device.

Referring now to FIG. 1, an eye exercising device is shown at 10 having an object in the form of a slide 12 which has an image formed thereon. A source light 16 and a diffuser 18 illuminate the image while a lens arrangement 20 focuses the image on the retina of the eye 22, which is to be positioned against an eye piece 24.

The slide is movable between positions "1" and "2" which are adjustable and selected according to the range of accommodation of the eye, as will be explained.

A motor unit 30 is provided to displace the slide 12 in a continuous fashion between positions "1" and "2", and is further provided with a calibrated adjustment knob 30*a* which enables the speed of movement of the slide to be varied according to the dynamic response of the visual accommodation system of the eye. A range adjustment knob 30*b* enables the adjustment of the distance between positions "1" and "2", while a dial 30*c* indicates the range of motion of the slide.

The lens arrangement 20 includes lenses 26 and 28, which are of an equal focal length, f, typically between 7 to 10 centimeters, and are spaced from the eye piece 24 according to dimensions "A" and "B", where "A" = f, "B" = 3f.

The spacing of the diffuser 18 from the lens 28 is also selected to avoid the diffuser from being focused on the eye.

During the operation of the eye exercising device 10, the subject's eye is positioned as indicated against the eye piece 24. The motor unit 30 is then activated causing the slide 12 to be oscillated smoothly and continuously between positions "1" and "2". Positions "1" and "2" are selected such that they lie just outside the proximal and distal limits respectively of the patient's range of accommodation. Typically, positions "1" and "2" are selected according to dimensions "C" and "D", where "C"=2f and "D"=3f/2. In addition, the lens arrangement 20 simulates position "1" to correspond to a dioptric distance of approximately 0 diopters, and position "2" to correspond to a dioptric distance of approximately 10 diopters.

During oscillation of the slide, the subject uses active concentration to attempt to maintain a clear focus of the image. This concentration is enhanced in the present embodiment by the bright illumination and detail of the photographic slide.

The effect of the movement of the slide on the eye will depend in part on the range of accommodation of the eye being exercised.

The eye exercising device 10 may be operated in a number of modes. In one mode, position "1" and position "2" are selected to lie just beyond the distal and proximal limits respectively of the range of accommodation of the subject's eye. The slide then moves from position "1" to position "2". Initially, there is a brief period of motion wherein the subject will be unable to focus on the image. During this period, the eye registers a blurry image of small size causing the ciliary muscle to attempt to relax. Subsequently the increasing size of the image on the retina and the change in blur cue indicate to the eye that the object is approaching the eye.

As the slide reaches the distal limit of the subject's range of accommodation, the image becomes clear while, subsequent displacement of the slide toward the eye causes a gradual contraction of the ciliary muscle to increase accordingly the convex shape of the lens. This process continues until the slide passes the proximal limit, at which point the image on the retina becomes blurred.

Shortly thereafter the slide 12 reaches position 2, the motor unit 30 reverses direction of the slide 12, thereby causing the object to move away from the eye. For a brief period, movement of the object toward the proximal limit causes little corresponding change in the eye since the image is blurred until the object passes the proximal limit. As the object continues to move away from the eye within the range of accommodation, the ciliary muscle relaxes gradually, thereby reducing gradually the convexity and thus the focal power of the lens. This movement and corresponding adjustment of the ciliary muscle continues until the slide reaches the distal limit, where the ciliary muscle is unable to relax further. However, the reduction of size of the image on the retina and the blur stimuli cause an enhanced effort to relax the ciliary muscle beyond the distal limit. The displacement of the slide continues slightly beyond the distal limit to position "1" where the direction is once again reversed to repeat the procedure.

A second mode of operation is also contemplated which enables the exercise to be concentrated in the region of the distal limit. In this case, position "1" is selected to lie outside the range of accommodation and just beyond the distal limit, while position "2" is selected to lie within the range of accommodation. The slide is then oscillated between positions "1" and "2" and thereby defines a single transition wherein the image becomes blurry or becomes clear, depending on the direction of travel of the slide.

A third mode analogous in operation to the second mode, is also contemplated wherein the exercise is concentrated at the proximal limit, rather than the distal limit.

It is to be emphasized that the repetitive procedure of bringing an image into and just out of focus combined with the appropriate increase and decrease in image size enables the eye to respond effectively to these cues, by gradually training the ciliary muscle to manipulate the lens.

The benefits of such a gradual training is defined in terms of an increase in the visual accommodation range of the subject. As the range of accommodation improves, positions "1" and "2" may be adjusted in the present embodiment such as to maintain said improvement and/or to expand further the range of accommodation. In this case, the range adjustment knob 30*b* is adjusted to vary the distance between positions "1" and "2".

A number of variations of the eye exercising device in FIG. 1 are contemplated, including the use of a computer 32 to monitor or adjust continuously or as required the type of motion (for example linear or sinusoidal), the rate of motion, the range of motion, and the frequency of motion cycles of the slide 12, to optimise the effectiveness of the device.

In this case, an infra-red optometer as is generally identified at 40 may be implemented, as is well known, to register the changes taking place within the eye.

The infra-red scanning unit 40 includes an infra-red reflective mirror element 40*a* which reflects infra-red light between an emitter-detector unit 40*b* and the subject's eye. The emitter-detector unit 40*b* in turn communicates with the computer 32 to transfer eye measurement data thereto.

Also contemplated is a biofeedback loop, by way of a tone generator 40*c* coupled with the emitter-detector unit 40*b* to provide an indication to the subject of the configuration of his eye.

Furthermore, additional lenses may be added to the device according to the specific requirements of a particular eye. For example, an attachment may be provided on the eye piece as identified at 34, in which a number of lenses may be interchanged as shown at 36, 38 to adjust the device rapidly to a particular eye. Alternatively positions "1" and "2" may be designated for the specific characteristics of each eye to be exercised.

Figure 2:
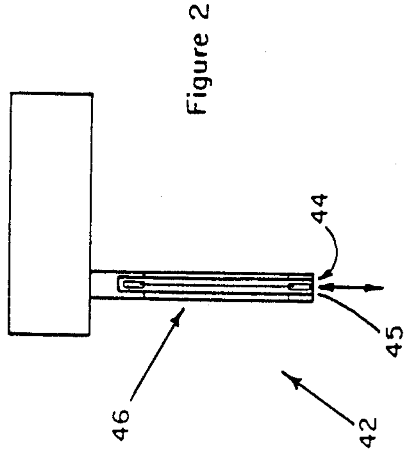
FIG. 2 is a schematic view of a portion of an alternative eye exercising device.

In addition, the slide 12 may be replaced after one or more oscillations, in order to maintain the interest of the subject, as is particularly important in the case of children. In this case, a slide assembly may be provided as shown at 42 in FIG. 2. The slide assembly 42 has a housing which forms a slide passage 44 for the insertion and removal of a slide 45 and an optical passage 46 for the passing of light through the slide 45 so as to form an image. Moreover, the optical path, shown as linear in FIG. 1, may be rendered more compact by the use of plane mirrors.

Figure 3:
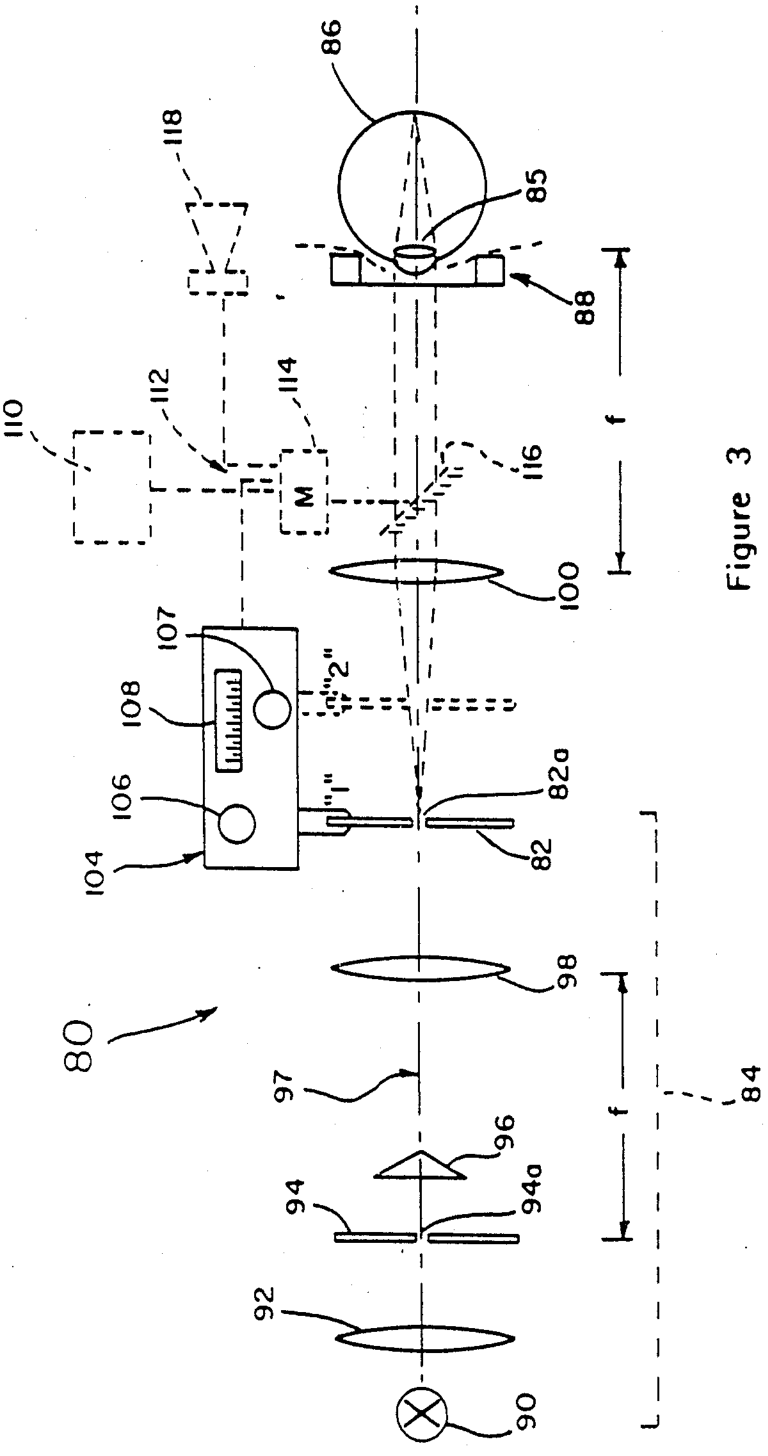
FIG. 3 is a schematic view of another eye exercising device.

In another embodiment as shown at 80 in FIG. 3, the image is seen in the form of a point of light as opposed to a visual image as in the above embodiments. The device 80 has a first plate 82 having a pinhole 82*a* and a projection arrangement as shown collectively at 84 to generate incident light on the pinhole 82*a* and to focus the light leaving the pinhole 82*a* on the lens of the eye shown at 86, in turn positioned against the eye piece 88.

The projection arrangement 84, known in the art as a Scheiner's image, includes a light source 90 and a first lens 92 which focuses the light to a plate 94 containing a second pinhole 94*a*. Pinhole 94*a* and a prism 96 create a pair of secondary light sources which are symmetrically disposed about the optical axis, identified at 97, and are focused at the lens 85 of the eye 86 by the lenses 98 and 100. Pinhole 94 is thus conjugate with the lens 85 of the eye 86.

If the diopter of the lens 85 of the eye 86 makes the retina of the eye 86 conjugate with pinhole 82*a*, the subject sees a single image of pinhole 82*a*. Otherwise, the subject sees two images whose separation, corresponding to the refraction of the lens of the eye 85, serves as a strong visual stimulus to the ciliary muscle to alter the shape of the lens of the eye to achieve a single image.

The first pinhole 82*a* is movable between positions "1" and "2" by way of a motor unit 104. The motor unit 104 includes speed adjustment knob 106, range adjustment knob 107 to adjust the range and speed of motion of the first slit plate 82 and a dial 108 to indicate such motion.

When operating the exercising device 80, pinhole 82*a* is oscillated smoothly and continuously between distal and proximal limits chosen for and adjusted to the range of accommodation of the particular eye being exercised. The separation of the images of pinhole 82*a* serves as an enhanced stimulus, thereby improving the concentration of the subject and thus the effectiveness of exercise. Moreover, in generating two distinct images, the device 80 provides a visual biofeedback to the subject, since the degree of accommodation varies with the degree of separation between the images.

As an alternative exercise, pinhole 82*a* may be located at the prior focal point of lens 100 with the subject being trained to relax the accommodative state of the eye according to an audio biofeedback method. Such audio biofeedback may be accomplished using an infrared optometer 112 incorporating infra-red emitter-detector unit 114 and an infra-red reflective mirror element 116. The optometer 112 completes the feedback loop to the subject by being connected to a tone generator 118.

It is envisaged that a combination of the two training methods (oscillation and biofeedback) described above can provide still greater advantage. Such combination of modes and actions is controlled by computer 110 which may be programmed to optimize subject concentration and rate and range of ciliary muscle exercise.

I claim:

1. A single eye exercising device comprising an optical path, positioning means to position said eye along said optical path, said optical path extending through at least one limit of the range of accommodation for the eye being exercised;

an image to be interrogated by said eye and movable along said optical path;

means to adjust the range of movement of said image along said path to cross said one limit;

displacement means to displace continuously and cyclically during exercise of the eye said image along said optical path between first and second locations on opposite sides of said limit whereby a continuously variable size and blur cue is provided to the eye being exercised.

2. A device as defined in claim 1 wherein said range of accommodation is defined between distal and proximal limits and said one limit is said distal limit.

3. A device as defined in claim 2 wherein said second location is wherein said range of accommodation.

4. An eye exercising device as defined in claim 2 wherein said second location is outside said range and is closer to the eye being exercised than said proximal limit.

5. An eye exercising device as defined in claim 1 wherein said range of accommodation is defined between a distal and a proximal limit and said one limit is said proximal limit.

6. An eye exercising device as defined in claim 5 wherein said second location is within said range of accommodation.

7. An eye exercising device as defined in claim 5 wherein said second location is outside said range and further from said eye being exercised than said distal limit.

8. An eye exercising device as defined in claim 1 wherein said image is provided by a photographic slide.

9. A eye exercising device as defined in claim 8 wherein said photographic slide is releasably engaged with said displacement means.

10. An eye exercising device as defined in claim 1, further comprising adjustable focusing means to facilitate the focus of said image on the lens of said eye.

11. An eye exercising device as defined in claim 10 wherein said focusing means includes a pair of lenses spaced apart between said positioning means and said object.

12. An eye exercising device as defined in claim 10 wherein said adjustable focusing means varies the focal point of said focusing means according to said range of accommodation of the eye being exercised.

13. An eye exercising device as defined in claim 1 wherein said image is generated by a plate having formed thereon an optical passage and an illumination means for casting light on said plate to form an image according to the shape of said passage.

14. An eye exercising device as defined in claim 13 wherein said passage is a small hole to generate said image in the form of a point of light.

15. A method of exercising a single eye comprising the steps of:

positioning said eye along an optical path, said optical path extending through at least one limit of the range of accommodation of said eye being exercised, said range of accommodation being delimited by a proximal limit and a distal limit;

providing an image to be interrogated by said eye on said optical path; and displacing said object continuously and cyclically along said optical path between first and second locations on opposite sides of said one limit to provide a continuously variable size and blur cue to the eye being exercised.

16. A method of exercising an eye as defined in claim 15 wherein said one limit is said distal limit.

17. A method of exercising an eye as defined in claim 16 wherein said second location is within said range of accommodation of the eye being exercised.

18. A method of exercising an eye as defined in claim 16 wherein said second location is outside said range of accommodation and closer to said eye than said proximal limit.

19. A method of exercising an eye as defined in claim 15 wherein said one limit is said proximal limit.

20. A method of exercising an eye as defined in claim 19 wherein said second location is within said range of accommodation of the eye being exercised.

21. A method of exercising an eye as defined in claim 19 wherein said second location is outside said range and further to said eye than said distal limit.

* * * * *